April 6, 1976 M. MEILLAND et al. Plant Pat. 3,857
ROSE PLANT - MEIBRICO VARIETY
Filed Oct. 24, 1974
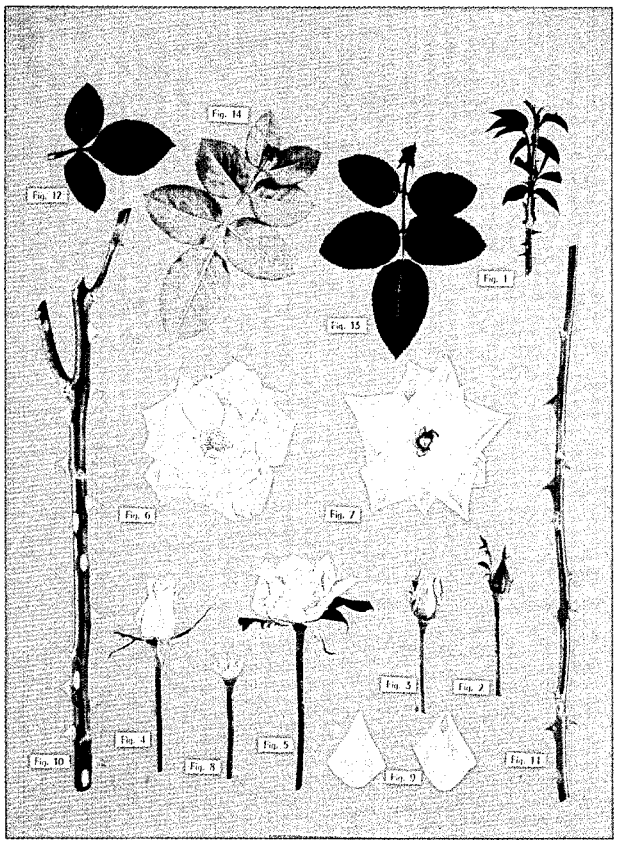

United States Patent

Plant Pat. 3,857

Patented Apr. 6, 1976

3,857

ROSE PLANT—MEIBRICO VARIETY

Marie-Louise Meilland and Alain A Meilland, Antibes, and Michele Meilland Richardier, Tassin-la-Demi-Lune, France, assignors to The Conard-Pyle Company, West Grove, Pa.

Filed Oct. 24, 1974, Ser. No. 517,821

Claims priority, application Morocco, Dec. 7, 1973, 16,625

Int. Cl. A01h *5/00*

U.S. Cl. Plt.—18 1 Claim

ABSTRACT OF THE DISCLOSURE

A new and distinct variety of rose plant of the hybrid tea class, especially for cut flowers, originated by crossing unnamed and unpatented seedlings, and obtaining a rich light coral color of its flowers.

SUMMARY OF THE INVENTION

The object of the present invention is a variety of rose-plant of the hybrid tea class, with orange-pink double flowers, which is distinguishable from varieties already known in that class and of that color, on account of the following characteristics:

Great originality of the rich light coral color of its flowers; and

Special aptitude of the plant to forcing, especially for a winter production of quality flowers.

Because of the above characteristics, the present invention answers the needs of the horticultural industry, for all uses, and more especially for the production of cut flowers.

The aim that the applicants had in view was to create a variety which would derive the aforementioned advantages from the genetic combination of two genitors whose previous and respective study would allow them to expect, in their common descent, the appearance of the characters sought.

The rose chosen as female genitor was an unpatented rose, the product of the pollination of the variety Meibrem–172F, more generally known in the trade under the name of Jolie Madame, by the variety Meisha–130F, more generally known in the trade under the name of Grisbi. The rose chosen as male genitor was an unpatented rose, the product of the pollination of the variety Memaj–542, more generally known in the trade under the name of Thais, by the variety Verla, more generally known in the trade under the name of Dr. Verhage.

The operation of artificial pollination performed by the applicants therefore can be expressed by the following schematic formula:

$$\frac{(\text{Meibrem–172F}}{(\text{Jolie Madame}} \times \frac{\text{Meisha–130F})}{\text{Grisbi}} \times \frac{(\text{Memaj–542}}{(\text{Thais}} \times \frac{\text{Verla})}{\text{Dr. Verhage)}}$$

From the fruits thus formed by this controlled pollination, seeds were extracted whose cells were the result of the combination of factors which existed in the cells of the genitors and in virtue of which these genitors had been precisely chosen.

After having sown these seeds, the applicants obtained 660 small plants, physically and biologically distinct from one another.

After having eliminated all the plants which were deficient or abnormal, or whose characters were too remote from the ones they were seeking, the applicants proceeded with the grafting of the remaining plants, in order to carry on their work exclusively on rose-plants which were, in every respect, in conformity with those produced and commercialized by professional nurserymen.

From then on, they undertook the selective study of the plants thus formed; during which study they were led to eliminate systematically all the rose-plants which had been grafted, with the exception of one only, which was the closest to the desired goal.

This variety had very well formed flowers, of a rich and very original light coral color, and asserted itself particularly suited for forcing.

Technical tests (grafting inside or outside, with dormant eye-buds, started eye-buds, in heated glasshouses, in cold glasshouses, on various understocks) were then made so as to ascertain the behavior of the variety just created.

The results were conclusive and underlined the importance of creating this variety with a view to its industrial exploitation, for all uses, especially for the winter production of cut flowers.

The characters and properties of this new variety, obtained as indicated above, are strictly transmissible by agamic means, also called "asexual," i.e. by any means of vegetative propagation, and in particular by grafting an "eye" which will be called in the trade by the name of eye of Meibrico–0853F and which will be found on industrial plants as well as on cut stems delivered subsequently in the trade. Thus will be obtained once again the new rose variety, whose botanical and descriptive characteristics, noted on plants under glass, are given below.

Asexual reproduction of this new rose by budding at West Grove, Pa., and in France, showed that the characteristics and distinctions come true to form and are established and transmitted through succeeding propagation.

BRIEF DESCRIPTION OF DRAWINGS

The accompanying drawings show as nearly true as it is reasonably possible to make the same in a color illustration of this character, typical specimens of flowers and foliage, illustrating in FIG. 1 is a specimen of a young shoot;

FIG. 2 is a specimen of a bud before the opening of the sepals;

FIG. 3 a specimen of a bud when sepals open;

FIG. 4 a specimen of bud when petals open;

FIG. 5 a specimen of a flower in the course of opening;

FIG. 6 a specimen of an open flower, flat view, upper surface;

FIG. 7 a specimen of an open flower, flat view, under surface;

FIG. 8 a specimen of a receptacle showing the disposition of the stamens and of the pistils;

FIG. 9 two specimens of petals from the outer periphery of the flower, the left one (upper surface) and the right one (under surface) showing the pointed tips and the lateral reflexed edges;

FIG. 10 a portion of a main branch;

FIG. 11 a portion of a flowering stem;

FIG. 12 a specimen of a leaf with three folioles, upper surface;

FIG. 13 a specimen of a leaf with five folioles, under surface; and

FIG. 14 a specimen of a leaf with seven folioles, upper surface.

DETAILED DESCRIPTION OF DISCLOSURE

The chart used for the identification of the colors is that of the Royal Horticultural Society (R.H.S. Color Chart). The terminology preceding the numbered references, proper to this chart, has been added to designate, in common terms, the corresponding colors.

Class: Hybrid tea.

Plant:

*Development.*—On the basis of cutting back the plants to about Om. 85, the length of the flowering stems to be cut can be said to reach between 60 to 90 cms.

*Habit.*—Straight.

Branches:

*Color.*—Young stems: before the buds are formed they are uniformly reddish purple; as and when buds develop, they still remain more or less reddish on the surface facing the sun, and turn to light green on the shaded parts. Mature wood: medium green 147/B after wiping out the "bloom" (powdery deposit).

*Prickles.*—Shape: fairly elongated and tapered. Upper edge: straight. Lower edge: concave. Base: obovate, narrow. Size: medium. Quantity: average—they are very often intermixed with needle-shaped point at the base of the branches. Color: on young stems: reddish purple. On mature wood: in succession reddish-pinkish straw, then Havana brown (common terms).

Leaves:

*Stipules.*—Adnate, pectinate, fairly wide and linear.

*Petiole.*—Obverse: the edges of the rib are reddish brown in the young foliage; medium green in the adult foliage and slightly grandular. Reverse: light green, with a few small hooked prickles. It forms, with the stem, an angle between 45° and 90°.

*Folioles.*—Number: 3–5–7. Shape: (starting from top, first pair of a leaf situated on the average ⅓ of a flower-bearing branch). Base: rounded, asymmetrical. Top: wide, symmetrical. General shape: elliptical. Teeth: single and fine. Texture: leathery. General effect: medium ample and dense foliage; shiny on young stems before the buds are formed, then, in succession, semi-mat and mat. Color: young foliage: Upper surface: bronze green. Under surface: light green more or less pigmented with reddish purple. Adult foliage: Upper surface; dark green 147/A (yellow-green group). Under surface: light green, between 191/A and 191/B (greyed green group).

It is to be noted that when growth starts, as also during the course of vegetation, the foliage of the young shoots is reddish purple on the upper and under surfaces.

Inflorescence:

*Number of flowers.*—One flower per stem.

*Peduncle.*—Straight, rigid, very slightly glandular, usually bronze green but also, sometimes, light green on shaded side, bronze green on sunny side. Length: from 8 to 10 cms.

*Sepals.*—Downy, greenish white inside; light green more or less spotted with reddish and smooth outside; the tips are narrow and tapered, the edges sometimes have quite a few appendages.

*Bud.*—Shape: pointed. Length: 32 mms. average, outside of calyx, at the opening of the first petal.

Size: medium. Color: when opening: Inside: orange 30/C (orange-red group). Outside: orange 29/A (orange-red group) more or less shaded with orange 32/C (orange-red group).

*Flower.*—Form: first of all, fully centered, protruding outside petals, enveloping and finally unfolded with pointed tips and reflexed lateral edges; then open in the shape of a cup; conspicuous stamens.

*Double flower.*—Diameter: 9 to 10 cms. Color: when opening: Inside: orange 30/C with a velvety shade of 30/B (orange-red group). Outside: yellow 13/B (yellow group) at base, washed with pinkish orange 29/B (orange group) and 29/A on the edge. During the course of opening: Inside: coral 32/B in depth, 32/C on the edges (orange-red group). Outside: yellow 13/B at base (yellow group) then gradually orange-pink 28/D at center and 28/C (orange group) in the folds of the lateral edges of the petals. When fully open: Inside: light coral 32/C in depth (orange-red group) with gleams of pink 38/A and 38/B (red group) on the edges; the general effect is, after all, light coral 32/D (orange-red group). Outside: yellow 15/D (yellow-orange group) at base, washed with pink 38/C towards the center, then pink 38/B (red group) in the folds of the lateral edges of the petals.

*Fragrance.*—Light.

*Lasting quality when cut.*—Long.

*Corolla.*—Petals: texture: firm; the unguis is yellow 13/B (yellow group). Shape: cuneiform base; very rounded tips; reflexed lateral edges. Number: an average of 30. The petals drop off cleanly. Stamens: number: 130 on an average. Anthers: normal; yellow. Filaments: yellow. Pistils: number: 80 on an average. Stigmas: yellowish; quite distinctly over the orifice of the receptacle and over the anthers. Styles: short; strangled and twisted when coming out of the receptacle, greenish yellow at base, reddish at the tips. Receptacle: light green, lengthwise and on a specimen chosen on a fully open flower, it is narrow and in the shape of a pitcher.

Development:

*Vegetation.*—Vigorous.

*Flowering.*—Practically continuous.

*Resistance to diseases.*—Is sometimes slightly sensitive to powdery mildew and botrytis.

We claim:

1. A new and distinct variety of rose plant of the hybrid tea class substantially as illustrated and described, distinguished as to novelty from the physical point of view: the plant, with medium green adult wood, is erect, the flower is double, coral inside, yellow and orange-pink outside, the petals are firm and show a yellow unguis; from the biological point of view: this rose plant grows vigorously, has great aptitude to forcing, its flowers last a long time when cut and the petals drop off cleanly.

No references cited.

ROBERT E. BAGWILL, Primary Examiner